United States Patent [19]

Kempe

[11] Patent Number: 5,648,271
[45] Date of Patent: Jul. 15, 1997

[54] METHOD FOR EVAPORATING SOLVENT USING FILTER

[75] Inventor: Tomas Kempe, Bowie, Md.

[73] Assignee: Barrskogen, Inc., Bowie, Md.

[21] Appl. No.: 279,444

[22] Filed: Jul. 25, 1994

Related U.S. Application Data

[63] Continuation-in-part of Ser. No. 209,786, Mar. 11, 1994.

[51] Int. Cl.$^6$ ........................................ G01N 1/00
[52] U.S. Cl. .................... 436/178; 436/177; 436/181; 422/100; 422/101; 422/103; 422/104; 159/6.1; 203/49; 203/86
[58] Field of Search ................... 422/68.1, 99, 100, 422/101, 102, 103, 104; 436/177, 181, 178, 180; 435/287, 298; 202/185.3, 237, 267.1; 159/6.1; 203/49, 86

[56] References Cited

U.S. PATENT DOCUMENTS

| | | | |
|---|---|---|---|
| 3,095,343 | 6/1963 | Berger | 156/180 |
| 3,111,702 | 11/1963 | Berger | 15/563 |
| 3,313,665 | 4/1967 | Berger | 156/180 |
| 3,957,588 | 5/1976 | Humiston | 202/172 |
| 4,003,713 | 1/1977 | Bowser | 422/101 |
| 4,346,057 | 8/1982 | Bowser | 422/101 |
| 4,683,195 | 7/1987 | Mullis et al. | 435/6 |
| 4,707,452 | 11/1987 | Friswell | 436/177 |
| 4,810,471 | 3/1989 | Wachob et al. | 422/103 |
| 5,100,623 | 3/1992 | Friswell | 422/68.1 |
| 5,156,811 | 10/1992 | White | 422/100 |
| 5,160,413 | 11/1992 | Allison | 422/101 X |
| 5,176,799 | 1/1993 | Roe et al. | 422/101 X |
| 5,217,572 | 6/1993 | Guy et al. | 159/6.1 |
| 5,364,595 | 11/1994 | Smith | 422/100 |
| B1 4,683,202 | 11/1990 | Mullis et al. | 435/91 |

OTHER PUBLICATIONS

Assortment of advertisements (undated) for "XCLUDA" aerosol barrier pipet tips (BioRad), Filtertips (hydrophobic polyethylene) (Eppendorf), Absolife filters (melt blown polypropylene) (Gelman Sciences), Aero–Gard brand aerosol barrier tips, Aeroshield filter pipet tips (Robbins Scientific), and Aeroseal Gold brand filter tips (USA Scientific Plastics, Inc.), two pages.

*Primary Examiner*—Harold Pyon
*Attorney, Agent, or Firm*—Fredrikson & Byron, P.A.

[57] ABSTRACT

A method for evaporating solvent in a manner that lessens the chance of cross-contamination between samples. The method involves the use of a filter material press fit into solvent-containing sample tubes. The material allows the flow through of evaporation while substantially preventing the flow through or loss of analyte. The method is particularly suitable for use in evaporative procedures involving vacuum, blow-down, and/or centrifugal processes.

13 Claims, No Drawings

METHOD FOR EVAPORATING SOLVENT USING FILTER

CROSS REFERENCE TO RELATED APPLICATIONS

This application is a continuation-in-part of application having U.S. Ser. No. 07/209,286, entitled APPARATUS FOR RAPID EVAPORATION OF AQUEOUS SOLUTIONS, filed Mar. 11, 1994.

TECHNICAL FIELD

The present invention relates to materials and methods useful for the evaporation of samples such as aqueous solutions, organic/water mixtures and the like. Such evaporation is commonly employed in biomedical laboratories for concentrating, purifying or recovering bioploymers such as DNA, RNA, peptides, proteins and saccharides.

BACKGROUND OF THE INVENTION

There presently exist several options for use in concentrating solutions used in biomedical research and development. Such solutions are aqueous in many instances, but may also frequently contain organic solvents that are miscible with water. Evaporation of organic solvents having low boiling points can often be performed rising a standard "rotavapor" type device.

Methods commonly used to remove water from solutions containing biopolymers often involve lyophilization or freeze drying. In such a method the sample is frozen in a tube or a flask, and a vacuum is applied. The removal of water is then performed from a solid state (e.g., ice) into a receiving flask, which is also cooled to collect the water vapor.

When an aqueous solution also contains an organic solvent that is miscible with water, it may not be possible to perform a lyophilization procedure, particularly if the mixture does not solidify upon cooling. In this case a number of other evaporation techniques can be used.

Such a solution can be subjected to a vacuum under conditions that prevent the sample from "bumping" (i.e., boiling in a manner that causes the solution to splash rapidly). The solution can then be agitated or rotated to generate a centrifugal force. Instruments suitable for such purposes can provide a combination of gyrating motion, heat, and either vacuum or blow-down. Certain instruments suitable for such purposes are generally referred to as centrifugal concentrators and are among the most common evaporators in laboratories.

With such evaporators, the evaporation process is generally facilitated by the use of a heating source, in fact, the vacuum chamber generally includes a thermostat-controlled heating device. The vacuum needed to use such evaporators is typically provided by the use of a high-vacuum pump that is capable of generating pressure down to at least 1 mm Hg.

A simple evaporation process can be achieved by the use of a heating block such as the "Reacti-Therm" dry block available from Pierce as product #18800/18801. In such a process a tube containing a sample is inserted into a block that can be heated to a desired temperature. A more efficient evaporation is achieved in the heated block if a gas is streaming through to carry the gaseous solvent with it. These types of evaporators are commonly called blow-down evaporators.

The evaporation units presently available, however, often encounter significant drawbacks. Generally, the evaporation units that are the least expensive and easiest to use are the same units that require the longest evaporation times, or have other associated drawbacks. In contrast, the more expensive and technically complicated units are often unnecessary for simple procedures and cost-prohibitive for many labs.

In response to these problems, Applicants have previously provided a simple and inexpensive, but highly effective, evaporation apparatus described in co-pending application Ser. No. 08/209,786. The apparatus is useful for evaporating solvents from a plurality of solvent-containing sample vials, and includes the use of a heat-transmissive block having a number of well positions that are used to hold sample vials within a chamber in the block.

The chamber can be covered by a cover to form a substantially air tight seal. The cover, in turn, has a corresponding number of access apertures for delivering air to the underlying vial. The block is also fitted with a vacuum system that can produce a vacuum within the chamber. The vacuum created within the chamber is used to pull air through the apertures and into the underlying vial, resulting in a combined vacuum/blow-down evaporative effect. Optionally, the block itself can be heated in order to further promote the process.

Generally each of the evaporation methods and apparatuses described above involve the use of tubes that are open to the ambient environment. Measures must often be employed to avoid or minimize cross-contamination between samples that may occur through bumping or splashing of the samples.

For instance, problems may arise when ammonium hydroxide is evaporated without pre-cooling, due to the high vapor pressure of ammonia. In such cases a strong vacuum can rapidly degas the solution in such a manner as to splash the contents from the vial and into the vacuum chamber. Bumping can also occur when the sample is cooled, since it is difficult to control the gaseous mist generated during the evacuation of the vacuum chamber used for the evaporation.

The evaporative effect created by a centrifugal vacuum evaporator is generally slow, as compared with a vacuum-blow down unit that furnishes a steady steam of air or inert gas through the vial or tube. This slower evacuation and concentration of the sample allows a gas-phase mist to equilibrate with the solution in the vial. As a result, however, biomolecules may be suspended in the mist, which potentially can enter and contaminate other tubes.

Many, if not all, biochemical procedures are quite sensitive to the problem of cross-contamination from adjacent or nearby sample tubes. For instance, ever-increasing sensitivity is provided by gene amplification techniques, such as the PCR technique described by U.S. Pat. Nos. 4,683,195 and 4,683,202 (Hoffmann La-Roche Inc.). Such techniques, however, require that the DNA sequences used in the reaction be completely free of other sequences. Otherwise, the PCR technique would tend to amplify any such contaminant in the final product.

In another context, quite distinct from evaporation, a number of products have been introduced over recent years for the prevention of aerosol contamination in the use of pipettes and pipette tips. Such products include "XCLUDA" aerosol barrier pipet tips from BioRad, FILTERTIPS (hydrophobic polyethylene) from Eppendorf, ABSOLIFE filters (melt blown polypropylene) from Gelman Sciences, AERO-GARD brand aerosol barrier tips, AEROSHIELD filter piper tips from Robbins Scientific, and AEROSEAL GOLD brand filter tips available from USA Scientific Plastics, Inc.

One such product for use in pipets is known as "ART" (aerosol resistant tips), available from Molecular Bio-Products (San Diego). Such tips are described in U.S. Pat. No. 5,156,811, the disclosure of which is incorporated herein by reference. This product is described as having a porous plug, formed of hydrophobic polyethylene, that is impregnated with particles of a liquid scavenging material. If any pores of the plug contact vaporized liquid droplets, the scavenging material swells so as to block gas or liquid flow through those particular pores.

What is clearly needed is an evaporation unit and method that provides an optimal combination of cost, ease of use, and efficiency for evaporating aqueous solvents commonly encountered in biomedical research.

SUMMARY OF THE INVENTION

The present invention provides a method of evaporating solvent from a tube containing a sample that comprises solvent and an analyte material, the method comprising the steps of:

(a) providing the sample in a tube of sufficient volume and dimensions to contain the sample in a lower region while providing a sample-free upper passageway region;

(b) providing a filter material having a longitudinal dimension capable of allowing flow through of evaporated solvent while substantially preventing the flow through of analyte material;

(c) inserting the filter material into a sealed and removable relationship to a predetermined distance into the tube passageway; and (d) evaporating the solvent in a manner that permits the flow through of solvent and substantially prevents the flow through of analyte material.

The method of the invention is particularly useful for both blow-down and centrifugal evaporation instruments, as well as those that combine the principles of blow-down and vacuum. With blow-down, for instance, a filter can be used that is capable of accepting a syringe needle or other gas delivery nozzle (e.g., pipet tip) to be sealably inserted through the length of the filter.

In another aspect, the invention provides a system useful for evaporating solvent from a sample containing solvent and an analyte material, the system comprising;

(a) a tube of sufficient volume and dimensions to contain the sample in a lower region and provide a sample-free upper passageway region;

(b) a filter material capable of allowing flow through for evaporated solvent while substantially preventing the flow through of vaporized analyte material;

the filter material being sealably and removably retained in the tube passageway.

In yet another aspect, the invention provides a filter material dimensioned to be sealably and removably inserted into an evaporation tube.

DETAILED DESCRIPTION OF THE PREFERRED EMBODIMENTS

The present invention provide a simple and inexpensive method for preventing or minimizing the chance of cross contaminations between samples in the course of evaporation processes. It has been discovered that the combination of a centrifuge tube or vial with a fast flow-through filter can provide an evaporation rate that is suitable for most purposes.

As used herein, the word "evaporate", and inflections thereof, will be used to refer to any form of a sample or its component parts, including gaseous phases, vapors, mists, and the like, having the potential to exit a tube in the course of an evaporative process. The word "analyte" will refer to any component of a sample (e.g., a biomolecule of interest) that is not intended to be lost from the sample in the course of an evaporation procedure.

We have discovered that fitting a conventional centrifuge tube or vial with a suitable filter in the manner described herein provides an effective barrier between the solution in the vial and the gas-phase mist in the evacuation chamber. Of equal importance, we have found that the porosity of the filter can be selected in a manner that does not unduly diminish the rate of evaporation. We have further found that the filter serves the added purpose of preventing contaminants from entering the tube.

In a preferred embodiment the tube is selected from the group consisting of microcentrifuge tubes and vials, as used in centrifugal evaporators and evaporations blocks, respectively. In a particularly preferred embodiment, the tube is a vial that is dimensioned to be used within an evaporating block, and the evaporation step is accomplished by a combined vacuum and blow-down process. High flow through filters of the type described herein are useful in evaporation processes such as the vacuum-blow down approach described in U.S. patent application Ser. No. 08/209,786. Such filters can dramatically reduce or even eliminate cross-contaminations between samples that are evaporated in the same unit at the same time.

Accordingly, the method of the invention is preferably accomplished using an apparatus comprising:

(a) a substantially heat-transmissive block having a top surface comprising a recessed sample chamber, the chamber comprising a plurality of well positions dimensioned to releasably hold sample vials in an upright, stable retained position within the chamber, (b) a positionable chamber cover dimensioned to form a substantially air tight seal when in a closed positioned upon the chamber, the cover comprising a plurality of access apertures, each dimensioned to receive a respective air channeling device and positioned to lay in substantially overlapping position with a respective well position when the cover is positioned upon the chamber, and (c) a vacuum circuit comprising a vacuum source attachment site associated with the block and a vacuum passageway operably connecting the source attachment site with the chamber, whereby, with solvent-containing vials in position within the chamber, a filter material can be positioned within the upper passageway of each vial. Air channeling devices, such as syringe needles, can then be positioned within the aperture of the cover and through the filter material. With the cover in position upon the chamber, and upon attachment of a vacuum source to the vacuum source attachment, a vacuum can be drawn in the sample chamber in such a manner that a gas is correspondingly drawn through the air channeling devices. The air flow is directed through the needles and toward the vial positions below in order to provide a blow-down evaporative effect. The evaporated gas/solvent mixture is capable of exiting each vial through the inserted filter as described herein.

In an alternative embodiment to the use of needles and cover septa, the filter material can be provided with a channel, e.g., centrally through the length of the filter. The channel can be used to contain and direct a piper tip passing through the cover (without a septum in place) and towards the sample tube. The pipet tip can optionally extend into or entirely through the filter material, so long as it forms a suitable seal with the material. Such a configuration lessens the risk associated with the use of needles, or the problems inherent in their disposal. In a further embodiment, the piper tip can itself be of the type that includes an internal filter (e.g., of the type described in U.S. Pat. No. 5,156, 811), thereby providing a complete filter seal for the tube passageway.

A number of other configurations are also possible using a pipet tip. For instance, the tip can be fitted with a sterile filter of a disc type in order to increase flow rate. Such an embodiment provides the benefits of both the pipet tip filter itself as well as the high flow rate achievable through the surrounding filter material, in order to keep the chance of cross contamination to a minimum.

Filter materials useful in the process of the present invention can be of any suitable type. Those skilled in the art will appreciate the manner in which filter-type materials developed for other purposes, such as cigarette filters and aerosol/fluid barriers for use in pipette tips, can be adapted to the method and system described herein. Examples of suitable materials include polyethylene, polypropylene, cellulose, cellulose acetate, polyester, polyurethane, latex sponge, and nylon. Examples of filters prepared using cellulose acetate fibers can be found, for instance, in U.S. Pat. Nos. 3,095,343, 3,111,702, and 3,313,665, the disclosures of which is incorporated herein by reference.

Preferred filter materials provide an optimal combination of such properties as porosity, hydrophobicity/hydrophilicity, throughput, swellability, inertness and cost. Additionally, preferred filter materials are capable of being extracted, in order to recover biomaterial that might come into contact with the material. Preferred materials are also stable to sterilization, such as by gamma radiation and heat sterilization.

Preferred filter materials for use with aqueous solutions can be of either hydrophilic or hydrophobic types. Hydrophilic types will tend to absorb water from an aqueous sample as it evaporates. Such absorption can lead to an increased rate of evaporation in view of the added capacity and absorbancy of the filter.

A preferred source of filter materials is the TRANSORB® brand media available from American Filtrona (Richmond, Va.). Such media are described as being prepared using either cellulose acetate, one or more polyolefins, or polyester, and was originally designed to address the phenomenon seen in surface filtration known as "straining." Straining occurs with membranes and other thin material filters when the main capture mechanism is the obstruction of particles larger than the pore size. This method can have certain advantages, primarily absolute particle size filtration. However, surface filtration devices have limited contaminant capacity which results in a rapid reduction in the flow rate and early "plugging."

The TRANSORB® filtration media is designed to include three capture mechanisms:

(1) Interception: Contaminants following flow streamlines around fibers touch the fibers as the streamlines compress around the fibers.

(2) Diffusion: Thermal and concentration gradients cause fine particles to fluctuate and hence enhance their capture.

(3) Inertial Interception: Due to their higher mass the particles deviate from flow streams and move towards the fibers.

The line of TRANSORB® brand media is available having porosity ranging from 70% to 92%. Although the "average" spacing between each fiber is much larger than the contaminant particle, typically an order of magnitude larger, the filters are still very effective in capturing small particles. While little contaminant capture occurs at the filter surface, the deeper the filter the higher the capture probability and the greater the filtration efficiency.

One advantages of the use of TRANSORB®—like media is the greater contaminant capacity and the high flow rates that can be achieved, since the open area is significantly greater than that of surface active filters.

TRANSORB media is said to be useful in such applications as: the removal of course particulates from membranes and hollow tube filtration; platelet separation in blood; fluid barriers for pipettes; heat-moisture exchange media for respiratory and ventilation systems; and aerosol filter media for disposable pipettes.

Different fiber types may have an affinity for specific fluid components, resulting in positive or negative effects. The selection of the correct fiber type best suited for the application will be well within the skill of those in the art, given the present description. Filter materials can be provided from bonded or unbonded fibers with a film, nonwoven, or paper wrapper as required. Consistent uniformity in physical dimensions facilitates handling and automated operations.

Such filters can also be coated on their exterior (i.e., tube contacting) surfaces with a polymeric material such as mylar. Such a coating will prevent or minimize the flow of evaporated solvents through the surfaces on the circumference of the material. As a result, the solvents will be restricted to flowing longitudinally, thereby providing a chimney-like effect.

For the evaporation of most organic solvents a hydrophilic filter prepared from bonded or unbonded polymeric binders is recommended, since a strong solvent may be capable of dissolving an organic polymer in the filter. With solutions that are entirely aqueous solutions or aqueous mixtures with organic solvents soluble in water, a hydrophilic filter such as cellulose acetate will be used together with similar hydrophobic materials as polyethylene, polypropylene, polyolefins, polyester, and the like.

Suitable materials can be designed and manufactured to serve as a filter material of the present invention, to include desired physical dimensions and filtration performance requirements. Bonded pre-filter media can be developed in most simple geometric cross-sections. Film wrapped pre-filter media can be made from acetate, nylon, or polyester fibers having no resin or adhesive binders. Such materials can be designed to provide particulate filtration in a nominal range of 10 to 100 microns for aqueous base fluids.

The filter material of the present invention can be produced as a plug to be press fit by a technician into any size vial or tube typically used for the evaporation of solvents and biomolecules. The filter can have the shape of a cone that can be snug-fitted in the opening. The filter can be incorporated into an open-cap that can be screwed on to the vial or tube, or the cap can be opened with a snap-on mechanism similar to that commonly used for microcentrifuge tubes. The filter can also be coated with a polymeric material in order to increase the filtration capacity.

Filter materials can be provided in any suitable dimensions, including width and length. Preferably, when used in conventional small volume vials or tubes, the filter material is generally cylindrical in shape. Such cylindrical materials will typically range from about 2 mm to about 35 mm, and preferably about 5 mm to about 15 mm, in diameter, and from about 5 mm to about 50 mm, and preferably about 10 mm to about 35 mm in final length. The length of the filter can be varied from minimum size of a typical surface filter that can be securely attached to the top with an open-top screw cap or snap on cap or having a length that by itself is sufficient to securely attach the filter to the top of the vial or tube by the restriction or friction between the filter and the wall of the vial or tube.

Increasing the longitudinal dimension of a filter will typically lessen the chance of cross-contamination potential to a point beyond which increased length is not likely to provide additional benefit. Those skilled in the art will understand the manner in which the optimal filter type and dimensions for a specific situation can be determined by judicious balancing of filter type and dimensions, solvent type, and the particular tube and method of evaporation employed.

Filters that be provided to users in longer lengths than necessary, e.g., on the order of 2–3 inches in length, which can then be easily cut by the users to a desired length for a particular evaporation routine.

Such filter materials can be used to prevent cross-contamination caused by a number of materials, such as solids (e.g. , particles), as well as mist- or gas-phase constituents such as simple organic molecules, polymers, radio-labelled samples, pathogens, viruses, bacteria, antigens, antibodies, specimen for diagnosis, blood, body fluids, and the like.

The filter of the invention serves as a barrier for potential contaminant outside the tube or vial as well as a barrier for retaining substances in the tube that have been solidified, dried or precipitated, thereby preventing cross-contamination of potential samples capable of leaving the tube. For instance, small solids formed or present in solution can otherwise be removed by turbulence or swirling movement in the chamber of a centrifugal evaporator, thus contaminating other samples when the solid is transferred to another tube.

The invention will be further described with reference to the following non-limiting Examples.

EXAMPLES

Example 1

Filters originally designed as cigarette filters were obtained from American Filtrona. The filters were produced from cellulose acetate fibers treated with a binder substance. Such filters were obtained in the following dimensions: 9.4 mm×30.67 mm long (R-15771); and 10.5 mm×27.74 mm long (R-15772). Filters of the first type were fitted into a polypropylene microcentrifuge tube of 1.5–2.0 ml size as well as into a glass vial 15 mm×45 mm, 4 ml size. Filters of the second type were fitted into a culture tube of 16 mm×100 mm, 12 ml size.

Evaporations of ammonia solutions were performed using an evaporation block vacuum-blow down unit of the type described in co-pending application Ser. No. 08/209,786. It was found that the evaporation times were similar with or without filters. The filters were inserted to a depth of about 10 mm into the vials, leaving about 20 mm extending above the vial top. In that configuration the top of the filter remained in close proximity to the closed cover of the evaporation unit. Needles were inserted through septa in the cover, and continuing through the filter material into each vial.

In one configuration, where incoming air was to be filtered, the needle female luer connector was fitted with a membrane filter of the type used in sterile filtration or particle filtration.

The needle tips were inserted to a point below the end of the filter. When vacuum was applied, impact of the incoming air could be seen upon ammonia solution in the vial. During the evaporation of ammonia and water, vapors travelled through the filter, before entering the vacuum chamber and finally leaving the chamber through the vacuum tubing.

The filter material demonstrated a number of desirable characteristics, including flow through that was sufficiently fast so as to not noticeably slow down evaporation; the ability to allow a needle to easily penetrate the length of the filter; and the ability to fit snugly into a 1.5–2.0 ml centrifuge tube typically used in centrifugal evaporators, as well as a 4 ml vial typically used in an evaporation block.

When used in a centrifuge tube the filter could be inserted about 25 mm leaving about 5 mm above the opening for easy removal with a forceps. The resistance against the centrifuge tube wall prevented the filter from sliding down during centrifugation. In the evaporation unit the filter was inserted about 10 mm into the vial. There it remained in close proximity to the cover, such that a needle could be inserted through a septa in the cover and through the filter. The needle tip remained below the filter end in the vial. When vacuum was applied the incoming air again stirred the solution in the vial, and evaporated solvent was able to leave the vial through the filter.

In both configurations, centrifuge tube and vial, there was a stream of solvent (solvent/air in the evaporation unit) flowing outward from within each container through the filter. Such a flow pattern serves to minimize or eliminate the introduction of a sample from one vial or tube to an other.

Example 2

A filter 9.6 mm in diameter and 20 mm long was prepared having a center channel of 2mm in diameter running the length of the filter. The filter was used in a vacuum blow-down evaporation unit in the following manner. The unit was fitted with 1.5 ml microcentrifuge tubes placed 5 mm below the lid surface. A solution of 0.5 ml solvent was placed in the tube. The filter was inserted to a depth of 15 mm into the tube, which was then placed into the unit.

The lid was replaced onto the unit (without the needle septum used in Example 1). Instead of a syringe needle, a pipet tip was placed into the hole through the lid, such that the tip extended into and partially through the channel in the filter, thereby sealing itself within the channel.

A vacuum was applied and the incoming air was introduced into the tube below via the piper placed in the channel filter. The outgoing air was able to pass through the filter material itself, as it entered the vacuum chamber and exited via the vacuum pump.

This Example demonstrates an alternative embodiment to the combination of septa, filter, and needle described in Example 1.

What is claimed is:

1. A method of evaporating solvent from a sample that comprises solvent and an analyte material, the method comprising the steps of:
   a) providing the sample in a unitary closed bottom tube of sufficient volume and dimensions to contain the sample in a lower region while providing a sample-free upper passageway region,
   b) providing a cylindrical filter material having a longitudinal dimension capable of allowing flow through of evaporated solvent while preventing the flow through of analyte material;

c) inserting the filter material into a sealed and removable relationship to a predetermined distance into the upper passageway region and positioning an air channeling device through the filter material;

d) positioning the tube into a device capable of drawing a vacuum on the tube and through the upper passageway region; and e) drawing a vacuum on the tube in order to evaporate solvent through the filter material in a manner which permits flow through of solvent and prevents flow through of analyte material, in order to solidify, dry or precipitate annlyte within the tube, and air flow is directed through the air channeling device to provide a blow-down evaporative effect.

2. A method according to claim 1 wherein the filter material is selected from the group consisting of cellulose acetate, polyolefin, and polyester, and is capable of providing a capture mechanism selected from the group consisting of interception, diffusion, and inertial interception.

3. A method according to claim 1 wherein the filter material is selected from the group consisting of polyethylene, polypropylene, cellulose, cellulose acetate, polyester, polyurethane, latex sponge, and nylon.

4. A method according to claim 3 wherein the filter material comprises cellulose acetate fibers.

5. A method according to claim 1 wherein the tube is a vial.

6. A method according to claim 5 wherein the vial is contained within an evaporating block, and the evaporation step is accomplished by a blow-down process.

7. A method according to claim 6 wherein the evaporation process is accomplished using an apparatus comprising:

(a) a heat-transmissive block having a top surface comprising a recessed sample chamber, the chamber comprising a plurality of well positions dimensioned to releasably hold sample vials in an upright, stable retained position within the chamber, b) a positionable chamber cover dimensioned to form an air tight seal when in a closed positioned upon the chamber, the cover comprising a plurality of access apertures, each dimensioned to receive a respective air channeling device and positioned to lay in overlapping position with a respective well position when the cover is positioned upon the chamber, and (c) a vacuum circuit comprising a vacuum source attachment site associated with the block and a vacuum passageway operably connecting the source attachment site with the chamber.

8. A method according to claim 7 wherein the filter material is positioned into each solvent-containing vial and the vials positioned within the chamber.

9. A method according to claim 7 wherein the cover is placed in position upon the chamber, and a vacuum is drawn in the sample chamber in such a manner that a gas is correspondingly drawn through the air channeling devices such that air flow is directed toward the vial positions below in order to provide a blow-down evaporative effect.

10. A method of evaporating solvent from a sample that comprises solvent and an analyte material, the method comprising the steps of:

a) providing the sample in a unitary closed bottom tube of sufficient volume and dimensions to contain the sample in a lower region while providing a sample-free upper passageway region, b) providing a cylindrical filter material having a longitudinal dimension capable of allowing flow through of evaporated solvent while preventing the flow through of analyte material;

c) inserting the filter material into a sealed and removable relationship to a predetermined distance into the upper passageway region;

d) positioning the tube into a device capable of drawing a vacuum on the tube and through the upper passageway region; and e) drawing a vacuum on the tube in order to evaporate solvent through the filter material in a manner which permits flow through of solvent and prevents flow through of analyte material, in order to solidify, dry or precipitate analyte within the tube, wherein the device is a centrifugal evaporator, the tube is a microcentrifuge tube useful in the evaporator, the filter material is press fit into the upper passageway of the tube in a manner that prevents it from sliding during centrifugation, the filter is a cylindrical filter having a diameter of about 2 mm to about 35 mm and a length of about 5 mm to about 50 mm, and the solvent is evaporated by the combined action of centrifugal force and vacuum drawn on the tube.

11. A method according to claim 10 wherein the filter material is selected from the group consisting of cellulose acetate, polyolefin, and polyester, and is capable of providing a capture mechanism selected from the group consisting of interception, diffusion, and inertial interception.

12. A method according to claim 10 wherein the filter material is selected from the group consisting of polyethylene, polypropylene, cellulose, cellulose acetate, polyester, polyurethane, latex sponge, and nylon.

13. A method according to claim 12 wherein the filter material comprises cellulose acetate fibers.

* * * * *